(12) United States Patent
Horeman

(10) Patent No.: US 11,197,686 B2
(45) Date of Patent: Dec. 14, 2021

(54) SURGICAL DEVICE

(71) Applicant: Surge-on Medical B.V., Delft (NL)

(72) Inventor: Tim Horeman, Delft (NL)

(73) Assignee: Surge-on Medical B.V., Delft (NL)

( * ) Notice: Subject to any disclaimer, the term of this patent is extended or adjusted under 35 U.S.C. 154(b) by 59 days.

(21) Appl. No.: 16/341,466

(22) PCT Filed: Oct. 17, 2017

(86) PCT No.: PCT/NL2017/050676
§ 371 (c)(1),
(2) Date: Apr. 12, 2019

(87) PCT Pub. No.: WO2018/074919
PCT Pub. Date: Apr. 26, 2018

(65) Prior Publication Data
US 2019/0298400 A1    Oct. 3, 2019

(30) Foreign Application Priority Data

Oct. 17, 2016 (NL) ...................... 2017630

(51) Int. Cl.
*A61B 17/29*  (2006.01)
*A61B 17/00*  (2006.01)
*A61B 34/00*  (2016.01)

(52) U.S. Cl.
CPC .............. *A61B 17/29* (2013.01); *A61B 34/71* (2016.02); *A61B 2017/00327* (2013.01);
(Continued)

(58) Field of Classification Search
CPC .......... A61B 17/29; A61B 2017/00318; A61B 2017/00323; A61B 2017/00327;
(Continued)

(56) References Cited

U.S. PATENT DOCUMENTS

| 2013/0172909 | A1 | 7/2013 | Harris |
| 2013/0200132 | A1* | 8/2013 | Moore ................ A61B 17/105 |
| | | | 227/180.1 |

(Continued)

FOREIGN PATENT DOCUMENTS

| DE | 4300307 A1 * | 7/1994 | ............. A61B 17/29 |
| DE | 4300307 A1 | 7/1994 | |

(Continued)

OTHER PUBLICATIONS

Dec. 13, 2017—ISR & WO—PCT/NL2017/050676.

*Primary Examiner* — Kathleen S Holwerda
*Assistant Examiner* — Uyen N Vo
(74) *Attorney, Agent, or Firm* — Banner & Witcoff, Ltd.

(57) ABSTRACT

The invention relates to a surgical device for minimally invasive surgery, comprising a shaft and a surgical module mounted to the distal end thereof. The shaft includes a tube and a pair of sliders driven by the tube via a rotary to linear linkage such that a rotation of the tube around the longitudinal axis induces a movement of the sliders along the longitudinal axis, in mutually opposite directions. The surgical device further includes wires that are each connected to a corresponding slider and to the surgical module such that a movement of the sliders, in mutually opposite directions, induces a movement of the surgical module in a first degree of freedom. The tube is also axially moveable towards the proximal end of the shaft inducing a movement of both sliders away from the surgical module, thereby inducing a movement of the surgical module in a second degree of freedom.

19 Claims, 7 Drawing Sheets

(52) U.S. Cl.
CPC ............... *A61B 2017/2902* (2013.01); *A61B 2017/2903* (2013.01); *A61B 2017/2927* (2013.01); *A61B 2017/2938* (2013.01)

(58) Field of Classification Search
CPC .... A61B 2017/2902; A61B 2017/2903; A61B 2017/2927; A61B 2017/2929; A61B 2017/2938; A61B 2017/2944; A61B 34/70; A61B 34/71
See application file for complete search history.

(56) References Cited

U.S. PATENT DOCUMENTS

| | | | |
|---|---|---|---|
| 2013/0267936 A1* | 10/2013 | Stroup | A61B 17/00234 606/1 |
| 2014/0005654 A1* | 1/2014 | Batross | A61B 34/30 606/33 |
| 2014/0005705 A1* | 1/2014 | Weir | A61B 34/30 606/169 |
| 2014/0277106 A1* | 9/2014 | Crews | A61B 34/35 606/205 |
| 2015/0105823 A1* | 4/2015 | Racenet | A61B 17/105 606/219 |
| 2015/0173756 A1* | 6/2015 | Baxter, III | A61B 17/064 227/177.1 |
| 2016/0008019 A1* | 1/2016 | Tuijthof | A61B 17/29 606/205 |
| 2016/0051318 A1* | 2/2016 | Manzo | A61B 18/1445 606/47 |
| 2016/0174976 A1* | 6/2016 | Morgan | A61B 34/30 227/175.1 |
| 2016/0302820 A1* | 10/2016 | Hibner | A61B 17/320092 |
| 2016/0303743 A1* | 10/2016 | Rockrohr | B25J 15/0233 |

FOREIGN PATENT DOCUMENTS

| | | |
|---|---|---|
| WO | 2012/078951 A1 | 6/2012 |
| WO | 2014/148898 A1 | 9/2014 |
| WO | 2016/057280 A2 | 4/2016 |
| WO | 2016/111621 A2 | 7/2016 |

* cited by examiner

SURGICAL DEVICE

CROSS-REFERENCE TO RELATED APPLICATIONS

This application is a U.S. National Stage application under 35 U.S.C. § 371 of International Application PCT/NL2017/050676 (published as WO 2018/074919 A1), filed Oct. 17, 2017, which claims the benefit of priority to Application NL 2017630, filed Oct. 17, 2016. Benefit of the filing date of each of these prior applications is hereby claimed. Each of these prior applications is hereby incorporated by reference in its entirety.

The invention relates to a surgical device for minimally invasive surgery, comprising a shaft having a longitudinal axis and extending between a proximal end and a distal end, further comprising a surgical module mounted to the distal end of the shaft and having at least two degrees of freedom, wherein the shaft includes a tube and a pair of sliders operatively driven by the tube via a rotary to linear linkage such that a rotation of the tube around the longitudinal axis induces a movement of the sliders along the longitudinal axis, in mutually opposite directions.

Typically, minimally invasive operations are performed through small portals for accessing deeper located tissue. During use of a known surgical device for minimally invasive surgery, the surgical module provided on the distal end of the shaft is brought into the body, via the portals, to manipulate said tissue. By interaction with the tube, at a proximal end thereof, a pair of sliders can be driven to induce a movement of the surgical module in one degree of freedom. In principle, multiple coaxial structures can be applied for moving the surgical module in more than one degree of freedom, in order to meet minimally invasive surgery purposes. However, due to the small size of the portals, the number of coaxial structures in the shaft for operating the surgical module is limited.

It is an object of the invention to provide a surgical device for minimally invasive surgery according to the preamble, wherein multiple degree of freedom operation of the surgical module is enabled with a relatively low number of coaxial structures in the shaft. Thereto, the surgical device according to the invention further includes a pair of wires that are each connected, at a proximal end thereof, to a corresponding slider and, at a distal end thereof, to the surgical module such that a movement of the sliders, in mutually opposite directions, induces a movement of the surgical module in a first degree of freedom, and wherein the tube is axially moveable along the longitudinal axis of the shaft towards its proximal end inducing a movement of both sliders along the longitudinal axis, away from the surgical module, thereby inducing a movement of the surgical module in a second degree of freedom.

By applying a pair of wires as an intermediate flexible structure for inducing movement of the surgical module, upon movement of the pair of sliders, a single tube can be used for inducing a surgical module movement in a first degree of freedom, viz. by rotating said tube to exert a pushing or pulling force to one of the wires, but also for inducing a surgical module movement in a second degree of freedom, viz. by shifting the tube, thereby exerting a pushing or pulling force on both wires.

Other advantageous embodiments according to the invention are described in the following claims.

By way of example only, embodiments of the present invention will now be described with reference to the accompanying figures in which FIG. 1 shows a schematic perspective view of a semifinished surgical device according to the invention including an inner rod and a tip assembly;

The figures merely illustrate a preferred embodiment according to the invention. In the figures, the same reference numbers refer to equal or corresponding parts.

Figure 1:
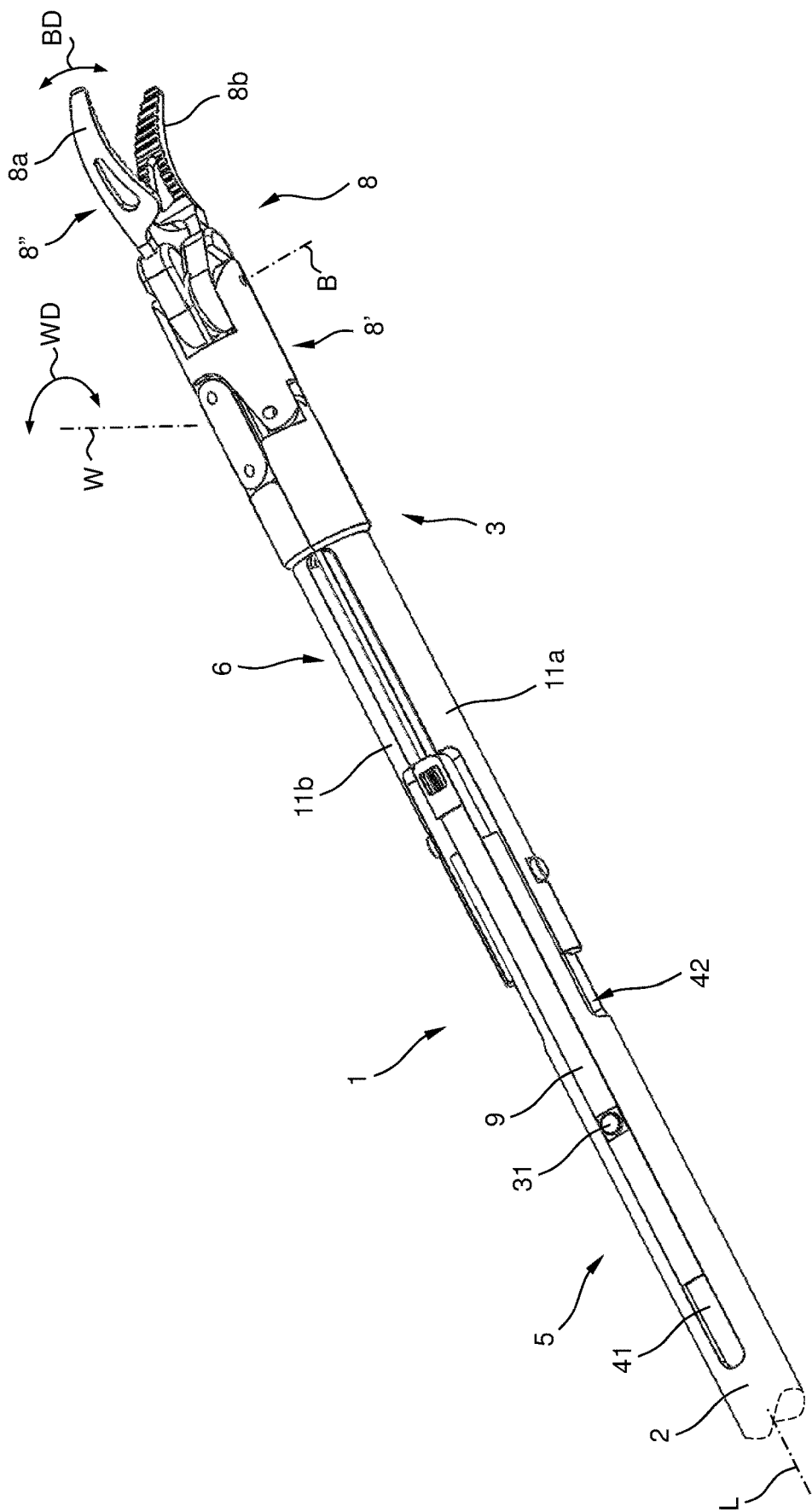

FIG. 1 shows a schematic perspective view of a semifinished surgical device 1 according to the invention including an inner rod 2 and a tip assembly 3, especially for use in minimally invasive surgery. Similarly, FIG. 2 shows a schematic perspective view of the semifinished surgical device 1 shown in FIG. 1 further including a first tube 4.

Generally, the surgical device 1 comprises a shaft 5 having a longitudinal axis L. The shaft 5 extends between a proximal end (not shown in FIG. 1) and a distal end G. Further, the surgical device 1 includes a surgical module 8 mounted to the distal end 6 of the shaft 5. In the shown embodiment, the surgical module 8 is a grasper having three degrees of freedom. The grasper has a wrist articulation portion 8' and a beak portion 8'' provided with two individually movable beak elements 8a,b.

Figure 2:
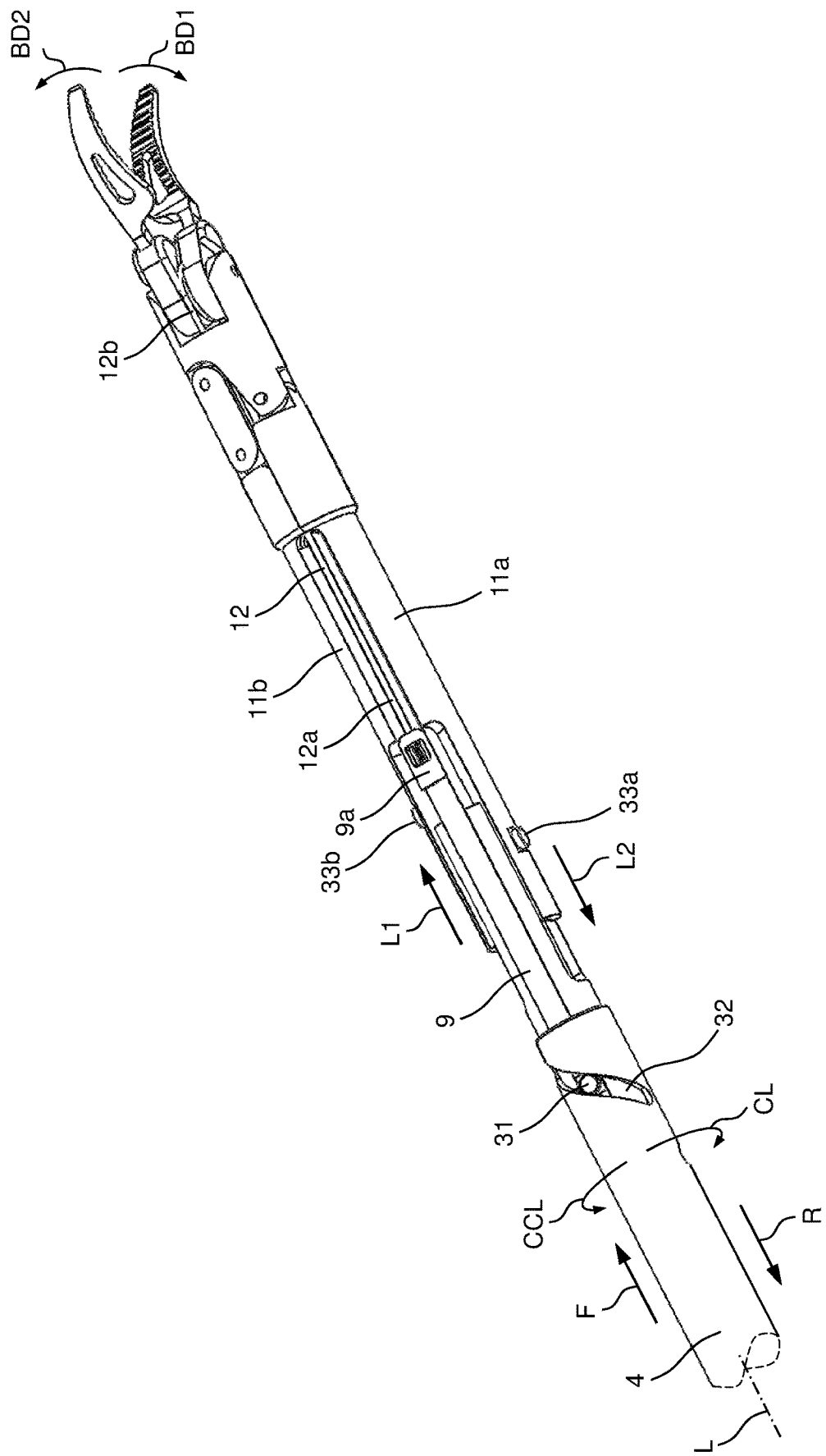
FIG. 2 shows a schematic perspective view of the semifinished surgical device shown in FIG. 1 further including a first tube.

The shaft 5 includes a first tube 4, shown in FIG. 2, for controlling movements of the grasper beak portion 8'' in a beak rotational direction BD around a beak axis B. The first tube 4 is coaxial with the inner rod 2 and has an inner diameter that is slightly greater than the outer diameter of the inner rod 2. As shown in FIG. 2, the first tube 4 surrounds the inner rod 2 along a portion thereof in the longitudinal direction L. The shaft 5 further includes a first pair of sliders 9 (only one slider is shown in FIGS. 1 and 2) that is operatively driven by the first tube 4 via a rotary to linear linkage such that a rotation of the first tube 4 around the longitudinal axis L induces a movement of the sliders 9 along the longitudinal axis L, in mutually opposite directions L1, L2.

In the shown embodiment, when the first tube 4 rotates clockwise CL, the visible slider 9 moves along the longitudinal axis L to the left L2, away from the surgical module 8, while the invisible slider moves along the longitudinal axis L to the right L1, towards the surgical module 8. Similarly, when the first tube 4 rotates counter clockwise CCL, the visible slider 9 moves along the longitudinal axis L to the right L1, towards the surgical module 8, while the invisible slider moves along the longitudinal axis L to the left L2, away from the surgical module 8.

Figure 3:
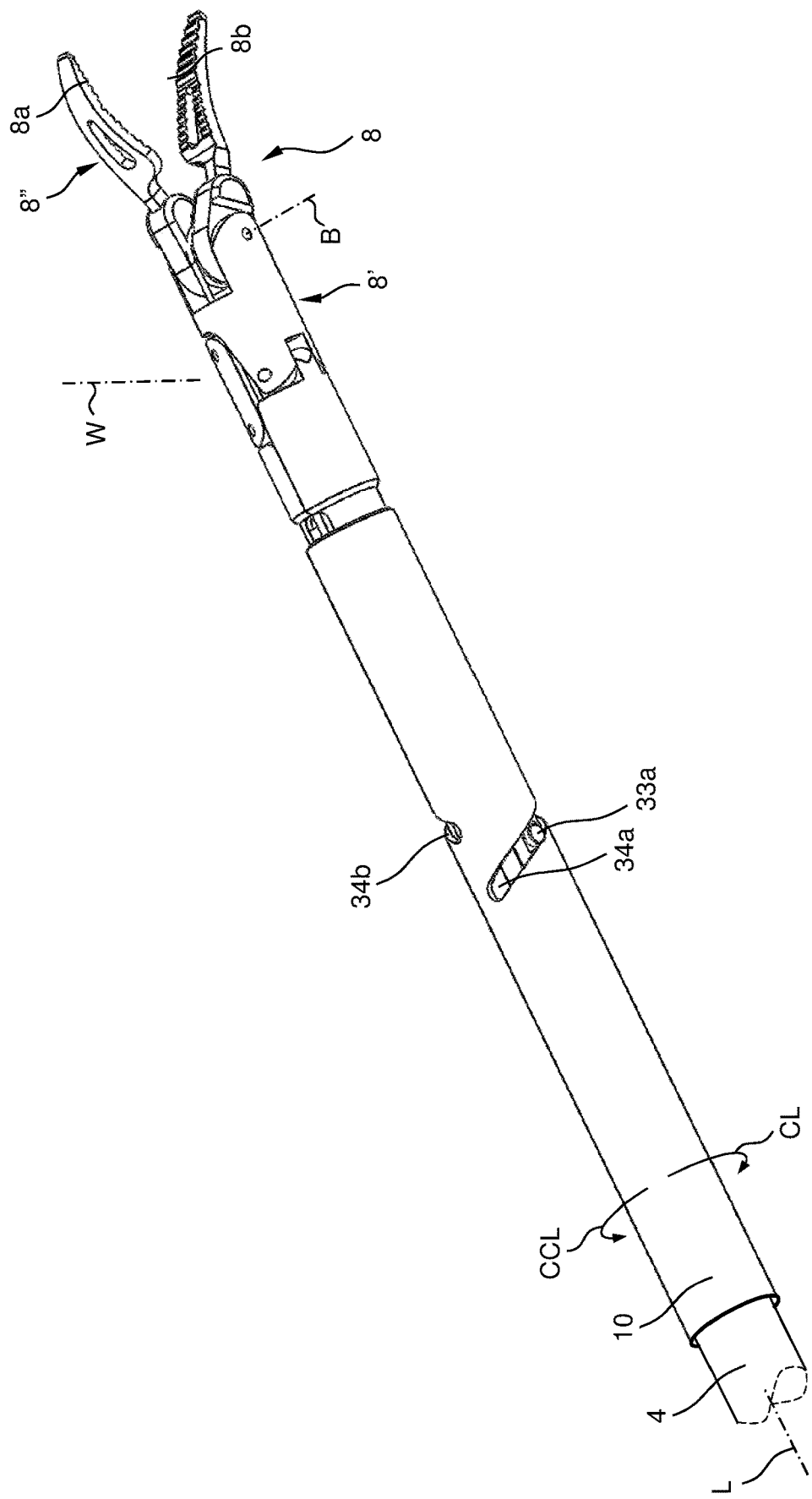
FIG. 3 shows a schematic perspective view of the semifinished surgical device shown in FIG. 1 further including a second tube.

FIG. 3 shows schematic perspective view of the semifinished surgical device shown in FIG. 1 further including a second tube 10. Here, the shaft 5 includes a second tube 10 that is coaxial with the first tube 4 and inner rod 2, and has an inner diameter that is slightly greater than the outer diameter of the first tube 4. As shown in FIG. 3, the second tube 10 surrounds the first tube 4 along a portion thereof in the longitudinal direction L. The shaft 5 further includes a second pair of slides 11a,b operatively driven by the second tube 10 via a second rotary to linear linkage such that a rotation of the second tube 10 around the longitudinal axis L induces a movement of the second pair of sliders 11a,b along the longitudinal axis L, in mutually opposite directions, inducing a movement of the wrist articulation portion 8' of the surgical module 8.

In the shown embodiment, similar to the structure of the first tube 4 and the first pair of sliders 9, when the second tube 10 rotates clockwise CL, a first slider 11a of the second pair of sliders moves along the longitudinal axis L to the left, away from the surgical module 8, while a second slider 11b of the second pair of sliders moves along the longitudinal axis L to the right, towards the surgical module 8. Similarly, when the second tube 4 rotates counter clockwise CCL, the first slider 11a of the second pair of sliders moves along the longitudinal axis L to the right, towards the surgical module 8, while the second slider 11b of the second pair of sliders moves along the longitudinal axis L to the left, away from the surgical module 8. The combined movement of the second pair of sliders 11 induces a movement of the wrist articulation portion 8' of the surgical module 8 in a wrist rotational direction around a wrist axis W.

The surgical device 1 further includes a pair of wires 12, also called flexors, that are each connected, at a proximal end 12a thereof, to a corresponding slider 9 and, at a distal end 12b thereof, to the surgical module 8 such that a movement of the sliders 9, in mutually opposite directions L1, L2, induces a movement of the surgical module 8 in a first degree of freedom. In the shown embodiment, when the visible slider 9 of the first pair of sliders moves to the right L1, both beak elements 8a,b turn in a first beak direction BD1. On the other hand, when the visible slider 9 of the first pair of sliders moves to the left L2, both beak elements 8ab, turn in a second beak direction BD2, opposite to the first beak direction BD1. Preferably, the proximal end 12a of a wire 12 is rigidly connected to a distal end 9a of the corresponding slider 9.

By rotating the first tube 4 around the longitudinal axis L a first wire 12 is subjected to a pushing force while a second wire 12 is subjected to a pulling force, via the first pair of sliders 9a,b, thus inducing a movement of the surgical module 8 in a first degree of freedom, in the shown embodiment, turning both beak elements 8a,b together in the same direction.

The first tube 4 is also axially moveable along the longitudinal axis L of the shaft 5 towards its proximal end inducing a movement of both sliders 9 along the longitudinal axis L, away from the surgical module 8, thereby exerting a pulling force on both wires and inducing a movement of the surgical module 8 in a second degree of freedom. In the shown embodiment, the beak elements 8a,b then turn towards each other, thereby realizing a beak closing movement. Similarly, when moving the first tube 4 axially along the longitudinal axis L of the shaft towards its distal end 6 a pushing force is exerted on both wires and both beak elements 8a,b then turn away from each other, thereby realizing a beak opening movement.

Then, by moving the first tube 4 along the longitudinal axis L, i.e. by shifting the first tube in a forward direction F or a rearward direction R, the beak portion 8" can be closed and opened. Further, by rotating the first tube 4, the beak portion 8" as a whole is turned. Thus, by properly operating the single, first tube, the surgical module 8 can controllably be moved in two degrees of freedom.

In the shown embodiment, the first pair of sliders 9, the second pair of slider 11a,b, the pair of wires and the surgical module 8 form the tip assembly 3 of the surgical device 1, or at least a portion of said tip assembly 3.

Figure 4:
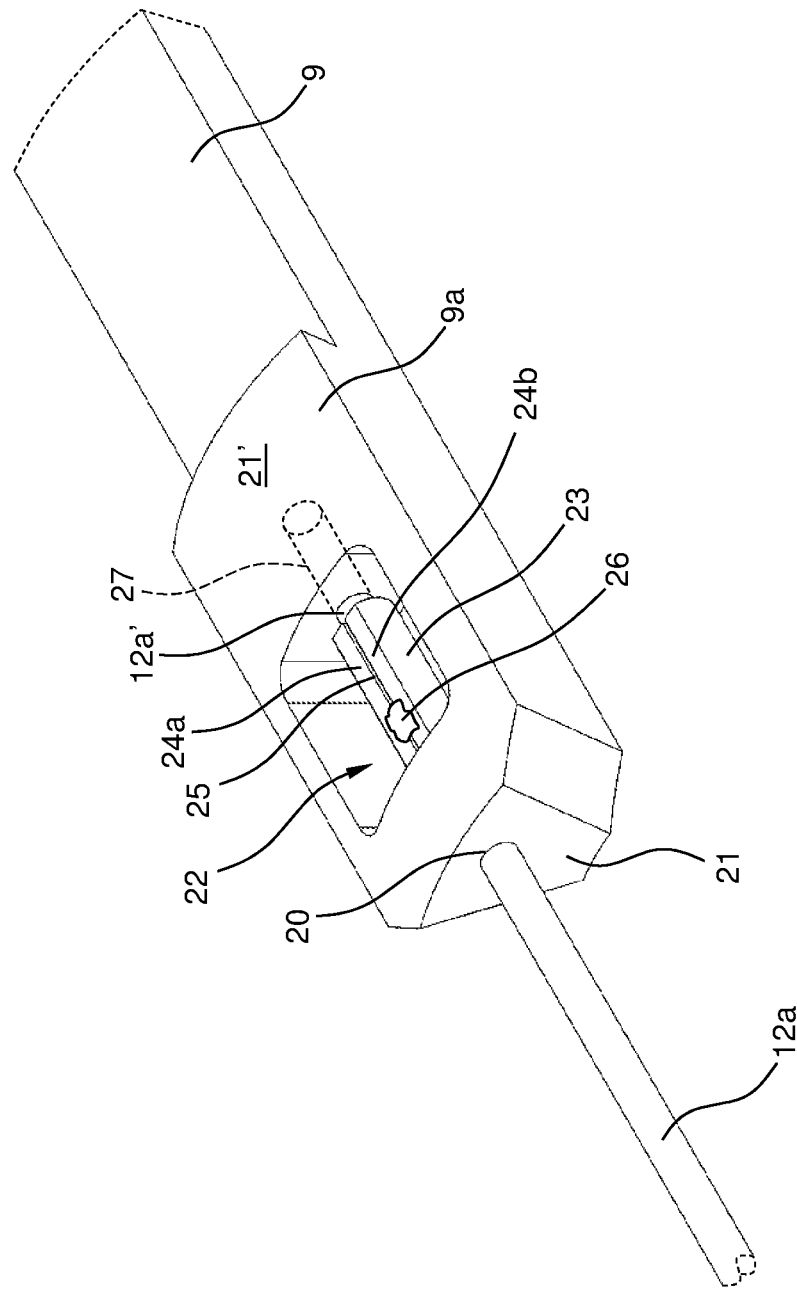
FIG. 4 shows a schematic perspective view of a connection structure of a wire and a slider in the surgical device shown in FIG. 1.

FIG. 4 shows a schematic perspective view of a connection structure of a wire 12 and a slider 9 in the surgical device 1 shown in FIG. 1. In the shown embodiment, the slider distal end 9a is block shaped having a slightly larger cross sectional area than a main portion of the slider 9. The slider distal end 9a is provided with an aperture implemented as a channel 20 extending from a front surface 21 to a cavity 22 provided in a top surface 21' of the slider distal end 9a. The cavity 22 includes a separate receiving unit 23 preferably formed as a single piece and preferably made from the same or similar material as the wire material, or made from another material that can be fixed to the wire in a reliable and rigid way. The receiving unit 23 supports and preferably at least partially surrounds the very proximal end 12a' of the wire 12. In the specific embodiment shown in FIG. 4, the receiving unit 23 is implemented as a tube element that is machined or chamfered along its longitudinal axis such that its interior is not completely enclosed by the tube material. The tube element includes a chamfered surfaces 24a,b and a contiguous slit 25 between them providing access from the exterior to the interior of the tube element 23. It is noted that the receiving unit 23 can be implemented in an alternative way, e.g. as a supporting structure having a C-shaped profile or as a tube having a closed circumferential contour. The proximal end 12a of the wire 12 extends into the aperture 20 in the slider distal end 9a, traversing the channel 20 and protruding into the cavity 22 such that the separate receiving unit 23 supports and/or receives said wire 12.

Advantageously, the wire 12 is made from nitinol, a medical certified material that has superior qualities for surgical application. Generally, nitinol can be sterilized relatively easily and can be subjected to high forces without being damaged. Advantageously, also the separate receiving unit 23 is made from nitinol.

During assembly of the connection between the wire 12 and the slider 9, the proximal end 12a of the wire 12 is inserted into the channel 20 penetrating the distal end 9a of the slider 9 until the very proximal end 12a' of the wire 12 is located in the receiving structure 23 in the cavity 22. Prior to a step of inserting the wire 12 into the aperture 20 and the cavity 22, the receiving unit 23 can be inserted into the cavity 22 of the slider distal end 9a. Then, preferably, the wire 12 is laser welded to the receiving unit 23 located in the cavity 22 of the slider distal end 9a, thereby obtaining a rigid connection between the wire proximal end 12a and the slider distal end 9a as the receiving unit 23 is locked against removal from the cavity 22. In the shown embodiment, welding material 26 is applied on the chamfered surfaces 24a,b of the receiving unit 23 and through the contiguous slit 25 on the wire 12 thereby interconnecting the receiving unit 23 and the nitinol wire extending through said receiving unit 23. Advantageously, the welding material 26 is provided along a substantial or mainly complete portion of the receiving unit 23, along its longitudinal dimension. In the shown embodiment, the distal end 9a of the slider 9 includes a further channel 27 extending from the cavity 22 opposite to the aperture 20 so that the wire 12 may extend through the aperture 20, through the cavity 22 and through further channel 27 to further improve the fixation of the connection. However, in principle, the slider distal end 9a can also be implemented without a further channel 27.

It is noted that, in principle, other or additional connection techniques can be applied for connecting the wire 12 to the slider 9, e.g. a clamping structure. It is further noted that the distal end 9a of the slider 12 can be implemented in another way, e.g. by providing a slider having a distal end with another geometry, e.g. including a transverse oriented pin connecting to the wire. In principle, the wire can be made from another material that is medically certified, e.g. a polymer material or a Stainless steel or tungsten cable. Further, the slider 9, or at least the distal end 9a of the slider 9, can be made from a metal such as stainless steel, or another material. In case bipolar energy is used to seal tissue during surgery, the beaks, cable and slider can be electrically isolated from the rest of metal components and can be used to transmit energy to the instrument beaks.

Figure 5:
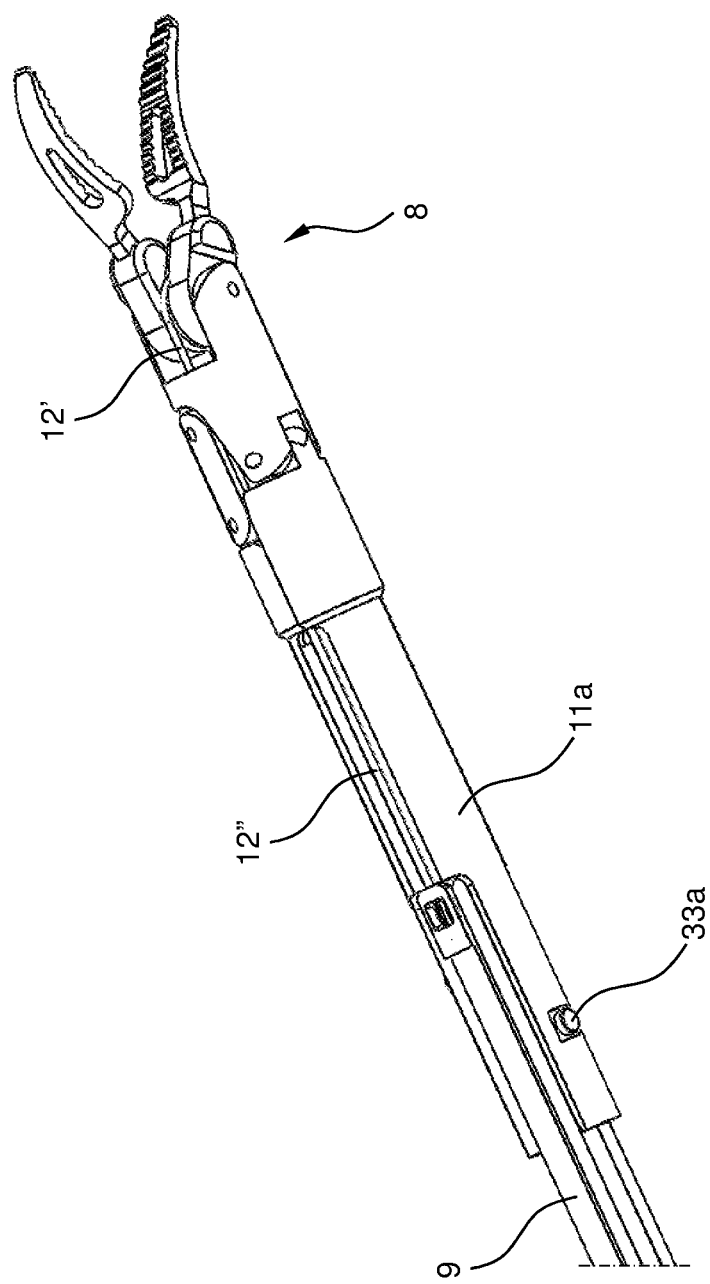
FIG. 5 shows a schematic perspective view of a tip assembly of the semifinished surgical device shown in FIG. 1.

FIG. 5 shows a schematic perspective view of a tip assembly 3 of the semifinished surgical device 1 shown in FIG. 1. Here, a slider 9 of the first pair of sliders, a slider 11a of the second pair of sliders, a wire 12 of the pair of wires, and the surgical module 8 are shown in an enlarged view.

Typically, the nitinol wires 12 extend along a mainly straight path from the slider distal end 9a towards a curved path section where the distal end 12b of the wire 12 is connected to surgical module 8. The connection between the wire distal end 12b and the surgical module 8 can be realized using a similar connection structure as the structure connecting the wire proximal end 12a to the corresponding slider 9. A distal end 12b of a first nitinol wire 12 can be rigidly connected to a first beak element 8a while a distal end of a second nitinol wire 12 can be rigidly connected to a second beak element 8b, preferably such that the distal end 12b of both wires 12 extend into an aperture of the corresponding beak element 8a,b or other corresponding element of the surgical module 8, similar to the connection structure described referring to the rigid connection between the wire proximal end 12a to the corresponding slider. Again, advantageously, the wire distal ends 12b can be laser welded to a separate receiving unit 23 provided in a cavity of the corresponding beak element 8a,b or other corresponding element of the surgical module 8.

Advantageously, a distal portion 12' of the nitinol wire 12 is pre-bent, in order to counteract high level mechanical stress in the nitinol wires. Further, a proximal portion 12" of the nitinol wire 12 is provided with stiffening material to counteract that the nitinol wires 12 flex at their proximal portion. Generally, the nitinol wire 12 is stiff enough to deliver a pushing force to the surgical module 8, but also flexible enough to follow a curved path in conformity with a swiveling movement that is performed by the connected beak element.

In the shown embodiment, the surgical module 8 is a grasper having three degrees of freedom, viz. a rotating movement of a wrist portion 8' around the wrist axis W, a rotation of the beak portion 8" around the beak axis B and a movement of opening and closing the beak portion 8". The grasper has a wrist articulation portion 8' and a beak portion 8" provided with two individually movable beak elements 8a,b. Here, each of the two individually beak elements 8a,b is connected to a corresponding wire 12. It is noted that the beak elements 8a,b can be replaced by other individually movable elements, such as cutting elements. Both individually movable elements can rotate around a common pivoting axis or around respective non-coinciding axes. The individually movable elements can be arranged for following another movement path, e.g. a linear path performing a translation. In another embodiment, a single piece of the surgical module might be movable in two degrees of freedom, operated by the single, first tube 4.

Further, the surgical module 8 may have more or less than three degrees of freedom, e.g. two degrees of freedom controllably operated by the single, first tube 4. Then, the surgical device 1 can be implemented without the second tube 10. In another embodiment, the surgical module 8 has more than three degrees of freedom, e.g. four degrees of freedom wherein also the second tube 10 is arranged for inducing a movement in two degrees of freedom.

The rotary to linear linkage may include a pin that extends from a first member into a radial direction of the shaft and cooperates with a spiral shaped slit in a second member for driving a first slider. Here, the first member can be a slider while the second member is a tube.

In the shown embodiment, the rotary to linear linkage driving the first set of sliders 9 includes a bayonet type connection using pins that are guided in spiral shaped slits. Here, each of both sliders 9 is provided with a pin 31 or other protrusion that extends radially outwardly. Further, the first tube 4 has two spiral shaped slits 32, also called fissures, each of the slits 32 cooperating with the pin 31 of a corresponding slider 9. During operation of the surgical device 1, the pin 31 extends into the corresponding slit 32 such that the pin 31 is locked in said slit 32 and can only follow a guiding path defined by said slit 32. Then, by rotating the first tube 4, the pin 31 is forced to travel in said slit 32, then moving along the longitudinal axis L to the right L1 or left L2, depending on the rotating direction of the first tube 4.

Preferably, the spiral shaped slits 32 in the first tube are located opposite to each other, in view of the longitudinal axis of the shaft 5, and have a mutually reversely oriented spiral shape, such that a rotation movement of the first tube 4 induces a balanced movement of the first pair of sliders 9, by inducing a first slider 9 to move to the right L1 and simultaneously inducing a second slider to move to the left L2, opposite to the right L1. Also the sliders 9 are located opposite to each other, in view of the longitudinal axis L of the shaft 5.

It is noted that, in theory, the bayonet type connection can be reversed, viz. in that the first tube includes racially inwardly protruding pins cooperating with spiral shaped slits in the sliders. Then, the above mentioned first member is the tube, while the second member is the slider.

The second rotary to linear linkage driving the second set of sliders 11 is implemented in a similar way, each of the second set of sliders 11 being provided with a pin 33a,b or protrusion that extends radially outwardly. Further, the second tube 10 has two spiral shaped slits 34a,b, each of the slits 34a,b cooperating with the pin 33a,b of a corresponding slider 11a,b. During operation of the surgical device 1, the pins 33a,b extend into the corresponding slits 34a,b such that the pins 33a,b are locked in said slits 34a,b and can only follow a guiding path defined by said slits 34a,b. Then, by rotating the second tube 10, the pins 33a,b are forced to travel in said slits 34a,b, then moving the sliders 11 along the longitudinal axis L to the right L1 and left L2, respectively, depending on the rotating direction of the second tube 10. Again, the sliders 11 are located opposite to each other, in view of the longitudinal axis L of the shaft 5.

The pitch of the spiral shaped slit can be uniform, i.e. constant along its bending profile. The value of the pitch can be selected between a relatively small value so that the corresponding pin moves relatively small when rotating the tube, and a relatively large value so that the corresponding pin moves relatively quickly when rotating the tube. Further, the pitch of the spiral shaped slit can be non-uniform, i.e. varying as a function of the circumferential position of the slit. As a consequence, also the speed of the pin varies when rotating the tube with a constant rotation speed. As an example, the pitch of the slit may decrease at an end portion of the slit such that the speed of the corresponding pin reduces when reaching an end of its guiding path.

In the shown embodiment, the inner rod 2 is provided, at its distal end, with pairs of cut-aways 41, 42 or recesses corresponding with the geometry of corresponding sliders 9, 11. During operation of the surgical device 1, the sliders of a pair of sliders 9, 11 is located in a corresponding cut-away in the inner rod 2, though movable relative to said inner rod 2 along the longitudinal axis thereof. The geometry of a cut-aways matches with the geometry of the slider that is located in said cut-away. Generally, the cut-aways have an elongate shape parallel to the longitudinal axis L of the shaft and the slider fits in said cut-away such that, at the axial level of the slider, a closed or mainly closed exterior circumferential contour is formed by the inner rod 2 and the sliders. During operation of the surgical device 1, the sliders are preferably supported by a local inner supporting structure of the inner rod 2 such that the sliders can not move radially inwardly in the shaft 5.

Preferably, the surgical device is demountable.

In a process of de-assembling the surgical device 1, the inner rod 2 is slightly retracted, in the rearward direction, relative to the first and second tube 4, 10, until the second pair of sliders 11a,b can move racially inwardly, thereby retracting the pins 33a from the corresponding slits 34a so as to enable the second tube 10 to be removed. Similarly, upon a further slight retraction of the inner rod 2 relative to the first tube 4, the first pair of sliders 9 can move racially inwardly, thereby enabling the first tube 4 to be removed.

Similarly, a process of assembling the surgical device includes a step of placing the first pair of sliders 9 in the corresponding cut-aways 41 in the inner rod 2, and a step of moving the first tube 4 in the forward direction F until the pins 31 of the first pair of sliders 9 lock into the corresponding slits 32 of the first tube 4. Then, the inner rod 2 is pushed in the forward direction F until a local inner supporting structure of the inner rod 2 blocks the sliders 9 to move racially inwardly in the shaft 5. The process further includes a step of placing the second pair of sliders 11 in the corresponding cut-aways 42 in the inner rod 2, and moving the second tube 4 in the forward direction F until the pins 33a,b of the second pair of sliders 11a,b lock into the corresponding slits 34a,b of the second tube 10. Again, the inner rod 2 can be pushed in the forward direction F until a local inner supporting structure of the inner rod 2 blocks the sliders 11 to move radially inwardly in the shaft 5.

Generally, the surgical device 1 includes a manual module that is connected to a proximal end of the shaft 5 for manually operating the surgical module 8 mounted to the distal end 6 of the shaft 5. The manual module typically includes manually displaceable elements such as rotation wheels controlling a relative axial position of the inner rod 2, the first tube 4 and the second tube 10, respectively, with respect to each other.

Figure 6A:
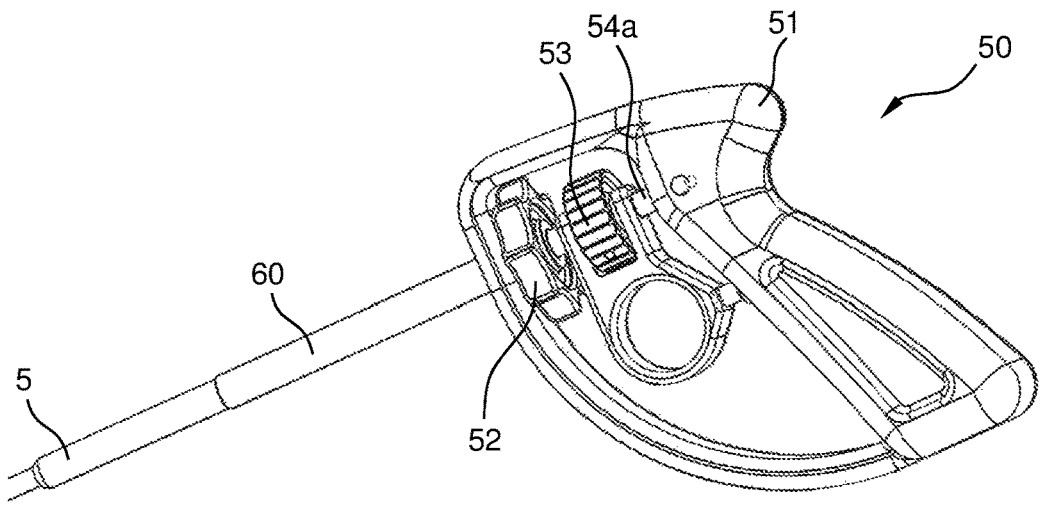
FIG. 6A shows a schematic perspective partial view of the surgical device shown in FIG. 3 wherein a shaft of the surgical device is connected to a manual module in a locked state.
Figure 6B:
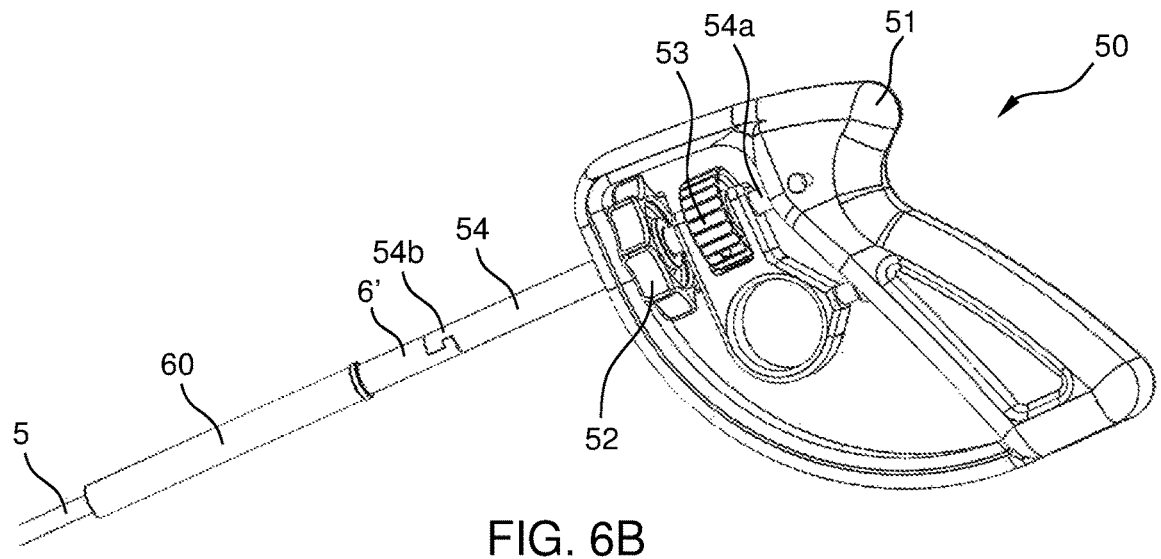
FIG. 6B shows a schematic perspective partial view of the surgical device shown in FIG. 6A wherein the shaft is connected to the manual module in an unlocked state.

FIG. 6A shows a schematic perspective partial view of the surgical device shown in FIG. 3 wherein a shaft 5 of the surgical device 1 is connected to a manual module 50 in a locked state. Similarly, FIG. 6B shows a schematic perspective partial view of the surgical device shown in FIG. 6A wherein the shaft 5 is connected to the manual module 50, however, in an unlocked state.

In the shown embodiment, the manual module 50 includes a handle 51 provided with manually displaceable elements implemented as rotation wheels 52, 53. Further, the manual module 50 includes a handle shaft 54 that is, at a proximal end 54a, driveably connected to the manually displaceable elements 52, 53 of the handle, and that is provided, at a distal end 54b, with a coupling profile 55a corresponding with a mating coupling profile 55b at the proximal end 6' of the shaft 5. The handle shaft 54 includes three concentric tubes having the same or similar radial size as the inner rod 2, the first tube 4 and the second tube 10. The three concentric tubes include an inner tube 56, an intermediate tube 57 and an outer tube 58, as shown in FIG. 6E described below. The coupling profile 55a of the handle shaft 54 is formed by three individual tube coupling profiles 56a, 57a, 58a of the concentric tubes 56, 57, 58 in the handle shaft 54, as described below in more detail referring to FIG. 6E. Similarly, the coupling profile 55b of the proximal end 6' of the shaft 5 is formed by three individual tube coupling profiles of the inner rod 2, the first tube 4 and the second tube 10, respectively.

When the shaft 5 is connected to the manual module 50, the coupling profiles 55a, 55b mate each other. Then, the three individual tube coupling profiles 56a, 57a, 58a of the concentric tubes 56, 57, 58 of the handle shaft 54 mate with the corresponding three individual tube coupling profiles of the inner rod 2, the first tube 4 and the second tube 10 of the shaft 5, such that the inner rod 2 is locked in axial and rotational movement, along the longitudinal axis L, with the inner tube 56 of the handle shaft 54, the first tube 4 is locked in axial and rotational movement with the intermediate tube 57 of the handle shaft 54, and the second tube 10 is locked in axial and rotational movement with the outer tube 58 of the handle shaft 54.

In the shown embodiment, the surgical device 1 further includes a coupling tube 60 surrounds or encloses the shaft 5 and/or the handle shaft 54. The coupling tube 60 can be shifted in the axial direction for racially locking and unlocking the connection between the shaft 5 and the handle shaft 54. When the shaft 5 and the manual module 54 are connected, the surgical device can be brought in a locked state, ready for operational use, by shifting the coupling tube 60 in the axial direction to a locking position such that the coupling tube GO surrounds both the shaft 5 and the handle shaft 54. Said locked state is shown in FIG. 6A. In the unlocked state, the coupling tube 60 is in an unlock position and only surrounds the shaft 5, and does not extend along the handle shaft 54. Then, the shaft 5 and the handle shaft 54 can be disconnected by removing them from each other in a radial direction. It is noted that, as an alternative, the coupling tube GO only encloses the handle shaft 54, in the unlocked state, not extending beyond the shaft 5. Advantageously, the coupling tube 60 may be fixed in axial position, at least in the locked state of the surgical device 1, to counteract that the connection between the shaft 5 and the handle shaft 54 is lost during use of the surgical device 1. Further, the coupling tube 60 may be biased to an axial position corresponding to the locked state, e.g. using a spring or another elastic member.

Preferably, the exterior radial size of the second tube 10 of the shaft 5 is the same or nearly the same as the exterior radial size of the outer tube 58 of the handle shaft 54, such that the coupling tube GO may shift along both the shaft 5 and the handle shaft 54 locking radial movement of the proximal end 6' of the shaft 5 relative to the distal end 54b of the handle shaft 54.

Figure 6C:
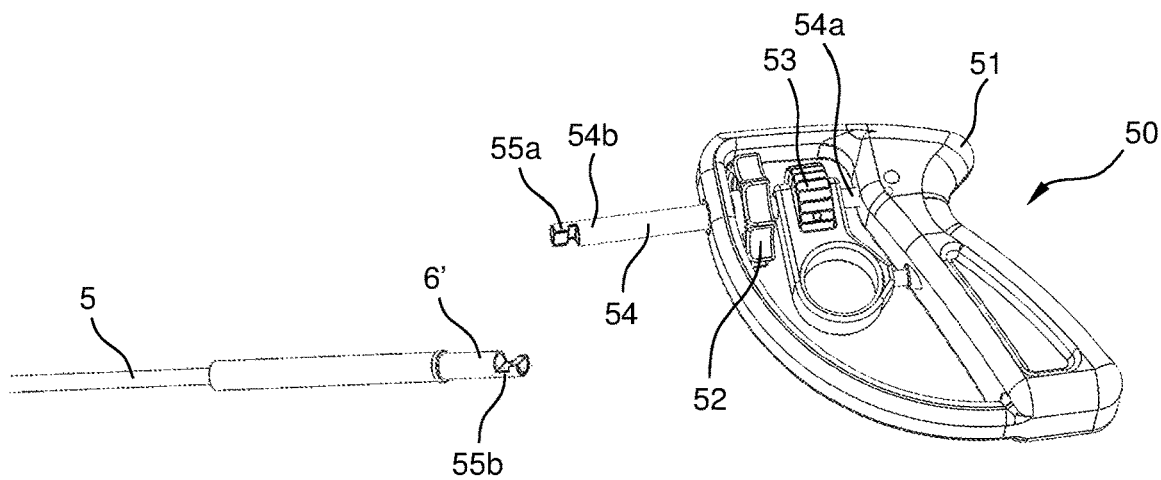
FIG. 6C shows a schematic perspective partial view of the surgical device shown in FIG. 6B wherein the shaft is disconnected from the manual module.

FIG. 6C shows a schematic perspective partial view of the surgical device shown in FIG. 6B wherein the shaft 5 is disconnected from the manual module 50.

Figure 6D:
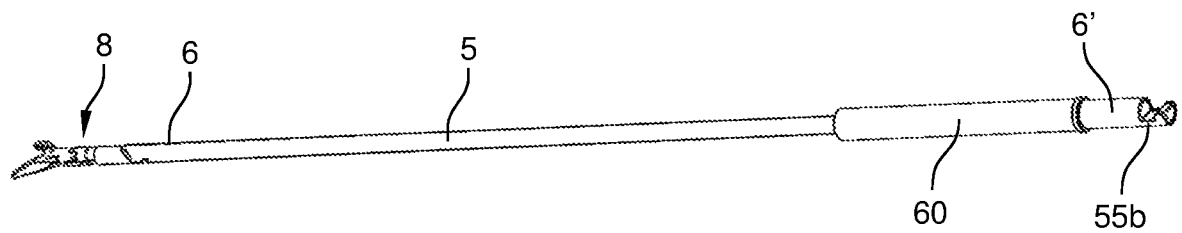
FIG. 6D shows a schematic perspective view of the shaft of the surgical device shown in FIG. 6C when disconnected from the manual module.
Figure 6E:
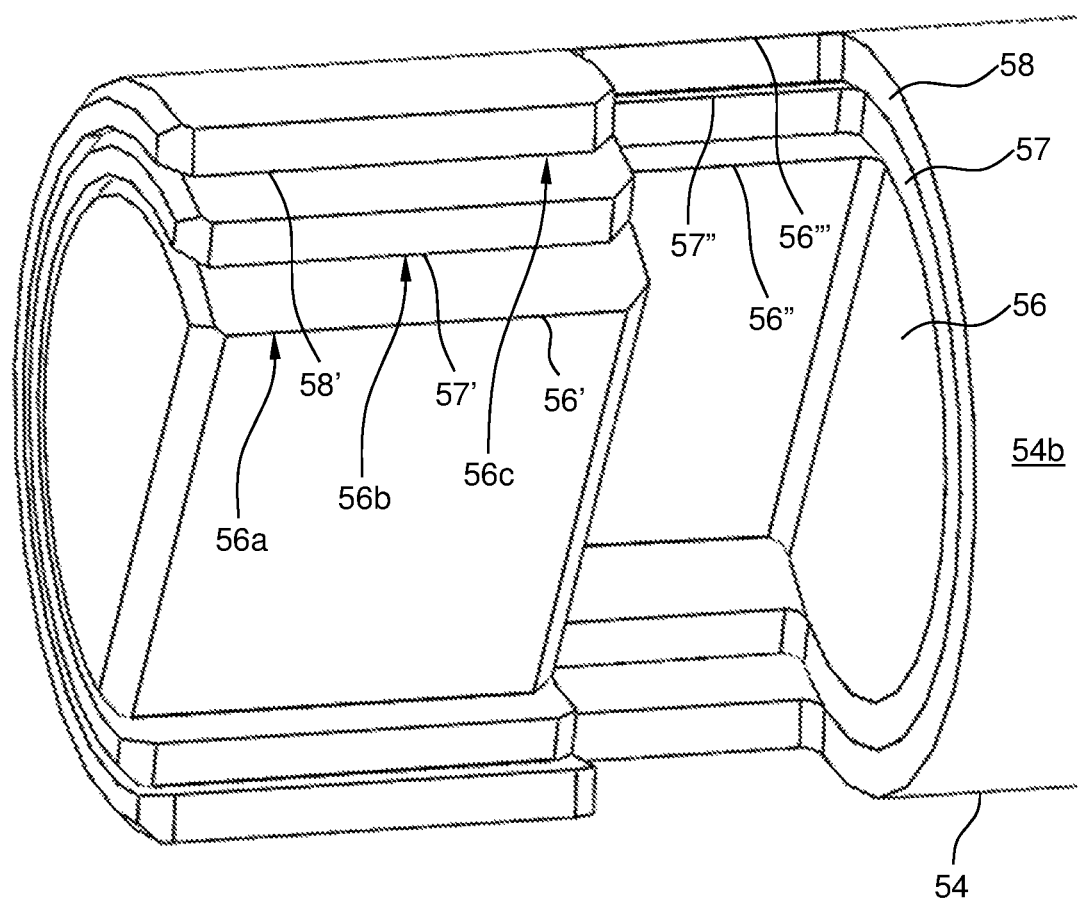
FIG. 6E shows a schematic perspective partial view of a connection structure of the manual module shown in FIG. 6A.

FIG. 6D shows a schematic perspective view of the shaft 5 of the surgical device 1 shown in FIG. 6C when disconnected from the manual module 50. Here, the entire shaft 5 is shown, as well as the surgical module 8 mounted to the distal end 6 of the shaft 5.

FIG. 6E shows a schematic perspective view of a distal end of the manual module shown in FIG. 6A. In FIG. 6E, the distal end 54b of the handle tube 54 is shown in more detail, including the inner tube 56, the intermediate tube 57 and the outer tube 58, and the corresponding three individual coupling profiles 56a, 57a, 58a described above. Preferably, the individual coupling profiles 56a, 57a, 58a are complementary with the corresponding coupling profiles of the inner rod 2, the first tube 4 and the second tube 10, respectively, such that in a connected assembly, the corresponding coupling profiles form an integral tube contour. In this context it is noted that the inner tube 56 of the handle tube 54 is preferably solid like a pin, i.e. not hollow but corresponding with the structure of the inner rod 2. In the shown embodiment, the individual coupling profiles 56a, 57a, 58a each have a racially extending tooth 56', 57', 58' engaging with a corresponding notch 56", 57", 58" in the corresponding coupling profile of the inner rod 2, the first tube 4 or the second tube 10.

In the shown embodiment, the concentric tubes 56, 57, 58 including their individual coupling profiles 56a, 57a, 58a may rotate and shift independently of each other, thereby independently controlling movement of the corresponding coupling profiles of the inner rod 2, the first tube 4 and the second tube 10, respectively.

The individual coupling profiles 56a, 57a, 58a can be formed by cutting a tube partly in a first radial direction, then cutting a first distance along an axial direction of the tube, then cutting a second distance in a second radial direction, opposite to the first radial direction, forming the notch 56", 57", 58", then cutting a third distance along the same axial direction as before, and then cutting in the first radial direction until the tube is completely cut, forming the tooth 56', 57', 58'. It is noted that the idea of locating the sliders in corresponding cut-aways provided in the inner rod can not only be used in a surgical device as defined in claim 1, but also, more generally, in a surgical device for minimally invasive surgery, comprising a shaft having a longitudinal axis and extending between a proximal end and a distal end, further comprising a surgical module mounted to the distal end of the shaft, wherein the shaft includes a tube and a pair of sliders operatively driven by the tube via a rotary to linear linkage such that a rotation of the tube around the longitudinal axis induces a movement of the sliders along the longitudinal axis, in mutually opposite directions, inducing a movement of the surgical module.

It is similarly noted that a process a assembling a surgical device by placing a first pair of sliders in corresponding cut-aways in the inner rod, and a step of moving a tube in the forward direction F until pills of the pair of sliders lock into corresponding slits of the tube, and a process of de-assembling a surgical device by slightly retracting an inner rod, in a rearward direction, relative to a tube until a pair of sliders can move radially inwardly, thereby retracting pins from the corresponding slits so as to enable the second tube to be removed can not only be applied to a surgical device according to claim 1, but also, more generally, in a surgical device for minimally invasive surgery, comprising a shaft having a longitudinal axis and extending between a proximal end and a distal end, further comprising a surgical module mounted to the distal end of the shaft, wherein the shaft includes a tube and a pair of sliders operatively driven by the tube via a rotary to linear linkage such that a rotation of the tube around the longitudinal axis induces a movement of the sliders along the longitudinal axis, in mutually opposite directions, inducing a movement of the surgical module.

It is further noted that the idea of coupling the distal end of the handle shaft to the proximal end of the shaft, using a coupling tube enclosing the shaft and the handle shaft can not only be applied to the surgical device according to claim 1, but also to a surgical device for minimally invasive surgery, comprising a shaft having a longitudinal axis and extending between a proximal end and a distal end, further comprising a surgical module mounted to the distal end of the shaft and having at least two degrees of freedom, wherein the shaft includes a tube and a pair of sliders operatively driven by the tube via a rotary to linear linkage such that a rotation of the tube around the longitudinal axis induces a movement of the sliders along the longitudinal axis, in mutually opposite directions. The number of concentric tubes in the handle shaft that are connected to corresponding tube structures in the shaft may be two, may be three as described above referring to FIG. 6A-E, or in principle, even more, e.g. four or five concentric tubes.

The invention is not restricted to the embodiments described herein. It will be understood that many variants are possible.

It is noted, as an example, that the rotary to linear linkages can, in principle, be implemented in another manner, e.g. using a screw linkage.

Further, the surgical device may include an actuation device, e.g. including an actuation wheel, for handling the first and/or second tube.

These and other embodiments will be apparent for the person skilled in the art and are considered to fall within the scope of the invention as defined in the following claims. For the purpose of clarity and a concise description features are described herein as part of the same or separate embodiments. However, it will be appreciated that the scope of the invention may include embodiments having combinations of all or some of the features described.

The invention claimed is:

1. A surgical device for minimally invasive surgery, comprising a shaft having a longitudinal axis and extending between a proximal end and a distal end, further comprising a surgical module mounted to the distal end of the shaft and having at least two degrees of freedom, wherein the shaft includes a tube and a pair of sliders operatively driven by the tube via a rotary to linear linkage such that a rotation of the tube around the longitudinal axis induces a movement of the sliders along the longitudinal axis, in mutually opposite directions, wherein the surgical device further includes a pair of wires that are each connected, at a proximal end thereof, to a corresponding slider and, at a distal end thereof, to the surgical module such that a movement of the sliders, in mutually opposite directions, induces a movement of the surgical module in a first degree of freedom, and wherein the tube is axially moveable along the longitudinal axis of the shaft towards its proximal end inducing a movement of both sliders along the longitudinal axis, away from the surgical module, thereby inducing a movement of the surgical module in a second degree of freedom, wherein the shaft includes a second tube and a second pair of sliders operatively driven by the second tube via a second rotary to linear linkage such that a rotation of the second tube around the longitudinal axis induces a movement of the second pair of sliders along the longitudinal axis, in mutually opposite directions, inducing a movement of the surgical module in a third degree of freedom.

2. The device of claim 1, wherein the proximal end of a wire of the pair of wires is rigidly connected to a distal end of the corresponding slider.

3. The device of claim 2, wherein the wire is made from nitinol.

4. The device of claim 2, wherein the proximal end of the wire extends into an aperture provided at the distal end of the corresponding slider.

5. The device of claim 4, wherein the proximal end of the wire is laser welded to a separate receiving unit provided in a cavity of the distal end of the corresponding slider, the separate receiving unit preferably being made from the same or similar material as the wire.

6. The device of claim 3, wherein a distal portion of the nitinol wire is pre-bent.

7. The device of claim 3, wherein a proximal portion of the nitinol wire is provided with stiffening material.

8. The device of claim 1, wherein the surgical module includes two elements that are connected to distal ends of the wires and are individually movable.

9. The device of claim 8, wherein the two elements are individually rotatable.

10. The device of claim 1, wherein the rotary to linear linkage includes a pin that extends from a first slider of the pair of sliders in a radial direction of the shaft and cooperates with a first spiral shaped slit in the tube for driving the first slider of the pair of sliders.

11. The device of claim 10, wherein the rotary to linear linkage includes a second pin that extends from a second slider of the pair of sliders in a radial direction of the shaft and cooperates with a second spiral shaped slit in the tube, for driving the second slider, wherein the first and second spiral shaped slits are located opposite to each other and have a mutually reversely oriented spiral shape.

12. The device of claim 10, wherein the pitch of the spiral shaped slit is non-uniform.

13. The device of claim 1, further including a manual module that is connected to the proximal end of the shaft for manually operating the surgical module mounted to the distal end of the shaft.

14. A surgical device for minimally invasive surgery, comprising a shaft having a longitudinal axis and extending between a proximal end and a distal end, further comprising a surgical module mounted to the distal end of the shaft and having at least two degrees of freedom, wherein the shaft includes a tube and a pair of sliders operatively driven by the tube via a rotary to linear linkage such that a rotation of the tube around the longitudinal axis induces a movement of the sliders along the longitudinal axis, in mutually opposite directions, wherein the surgical device further includes a pair of wires that are each connected, at a proximal end thereof, to a corresponding slider and, at a distal end thereof, to the surgical module such that a movement of the sliders, in mutually opposite directions, induces a movement of the surgical module in a first degree of freedom, and wherein the tube is axially moveable along the longitudinal axis of the shaft towards its proximal end inducing a movement of both sliders along the longitudinal axis, away from the surgical module, thereby inducing a movement of the surgical module in a second degree of freedom, wherein the rotary to linear linkage includes a pin that extends from a first slider of the pair of sliders in a radial direction of the shaft and cooperates with a spiral shaped slit in the tube for driving the first slider of the pair of sliders, the device further comprising an inner rod that is coaxial with the tube, the first tube having an inner diameter that is slightly greater than the outer diameter of the inner rod, the inner rod being provided with a local inner supporting structure such that, in an operation position of the inner rod, the sliders can not move radially inwardly in the shaft locking the pin in the spiral shaped slit, while in a retracted position of the inner rod, along the longitudinal axis of the shaft, the sliders can move radially inwardly in the shaft retracting the pin from the spiral shaped slit.

15. A surgical device for minimally invasive surgery, comprising a shaft having a longitudinal axis and extending between a proximal end and a distal end, further comprising a surgical module mounted to the distal end of the shaft and having at least two degrees of freedom, wherein the shaft includes a tube and a pair of sliders operatively driven by the tube via a rotary to linear linkage such that a rotation of the tube around the longitudinal axis induces a movement of the sliders along the longitudinal axis, in mutually opposite directions, wherein the surgical device further includes a pair of wires that are each connected, at a proximal end thereof, to a corresponding slider and, at a distal end thereof, to the surgical module such that a movement of the sliders, in mutually opposite directions, induces a movement of the surgical module in a first degree of freedom, and wherein the tube is axially moveable along the longitudinal axis of the shaft towards its proximal end inducing a movement of both sliders along the longitudinal axis, away from the surgical module, thereby inducing a movement of the surgical module in a second degree of freedom, the device further including a manual module that is connected to the proximal end of the shaft for manually operating the surgical module mounted to the distal end of the shaft, wherein the manual module includes a handle and a handle shaft that is provided, at a distal end, with a coupling profile corresponding with a mating coupling profile at the proximal end of the shaft, the device further comprising a coupling tube that is axially movable between a lock position wherein the coupling tube surrounds the shaft and the handle shaft, and an unlock position wherein the coupling tube surrounds the shaft only or the handle shaft only.

16. The device of claim 15, wherein the coupling profile of the handle shaft is formed by individual tube coupling profiles of concentric tubes in the handle shaft.

17. The device of claim 15, wherein the coupling profile includes a tooth engaging with a notch in the corresponding mating coupling profile.

18. The device of claim 15, wherein the rotary to linear linkage includes a pin that extends from a first slider of the pair of siders into a radial direction of the shaft and cooperates with a spiral shaped slit in the tube for driving the first slider of the pair of sliders.

19. The device of claim 15, wherein the shaft includes a second tube and a second pair of sliders operatively driven by the second tube via a second rotary to linear linkage such that a rotation of the second tube around the longitudinal axis induces a movement of the second pair of sliders along the longitudinal axis, in mutually opposite directions, inducing a movement of the surgical module in a third degree of freedom.

\* \* \* \* \*